(12) United States Patent
Kownacki et al.

(10) Patent No.: US 9,108,994 B2
(45) Date of Patent: Aug. 18, 2015

(54) (TRIORGANOSILYL)ALKYNES AND THEIR DERIVATIVES AND A NEW CATALYTIC METHOD FOR OBTAINING NEW AND CONVENTIONAL SUBSTITUTED (TRIORGANOSILYL)ALKYNES AND THEIR DERIVATIVES

(75) Inventors: Ireneusz Kownacki, Poznan (PL); Bogdan Marciniec, Swarzedz (PL); Beata Dudziec, Poznan (PL); Agnieszka Kownacka, Poznan (PL); Mariusz Majchrzak, Poznan (PL); Mateusz Szulc, Krosno Odrzanskie (PL); Bartosz Orwat, Wolsztyn (PL)

(73) Assignee: ADAM MICKIEWICZ UNIVERSITY, Poznañ (PL)

( * ) Notice: Subject to any disclaimer, the term of this patent is extended or adjusted under 35 U.S.C. 154(b) by 203 days.

(21) Appl. No.: 13/976,260

(22) PCT Filed: Dec. 29, 2011

(86) PCT No.: PCT/PL2011/050056
§ 371 (c)(1),
(2), (4) Date: Sep. 5, 2013

(87) PCT Pub. No.: WO2012/091588
PCT Pub. Date: Jul. 5, 2012

(65) Prior Publication Data
US 2014/0005427 A1     Jan. 2, 2014

(30) Foreign Application Priority Data

Dec. 30, 2010 (PL) .......................... 393475
Dec. 30, 2010 (PL) .......................... 393476
Apr. 6, 2011 (PL) .......................... 394454
Dec. 24, 2011 (PL) .......................... 397507

(51) Int. Cl.
*C07F 7/08* (2006.01)
*C07F 13/00* (2006.01)
*C07F 7/18* (2006.01)
*C07F 17/02* (2006.01)
*C07F 7/10* (2006.01)

(52) U.S. Cl.
CPC .............. *C07F 13/00* (2013.01); *C07F 7/0809* (2013.01); *C07F 7/0818* (2013.01); *C07F 7/0827* (2013.01); *C07F 7/0856* (2013.01); *C07F 7/0869* (2013.01); *C07F 7/0887* (2013.01); *C07F 7/10* (2013.01); *C07F 7/188* (2013.01); *C07F 7/1852* (2013.01); *C07F 7/1856* (2013.01); *C07F 7/1864* (2013.01); *C07F 7/1876* (2013.01); *C07F 7/1892* (2013.01); *C07F 17/02* (2013.01)

(58) Field of Classification Search
CPC .............................. C07F 13/00; C07F 7/1876
USPC ........................................................ 556/11
See application file for complete search history.

(56) References Cited

U.S. PATENT DOCUMENTS

2009/0318726 A1* 12/2009 Marciniec et al. ............ 556/478

FOREIGN PATENT DOCUMENTS

JP         A-8-92257         4/1996
WO    WO 2008/020774 A1    2/2008

OTHER PUBLICATIONS

Bolourtchian, M. et al., "Synthesis of *Bis*trimethylsilylated Hydroxy Alkynes," *Monatshefte für Chemie Chemical Monthly*, 1999, pp. 333-336, vol. 130.
Arcadi, A. et al., "Palladium-Catalysed Reductive Addition of Aryl Iodides to Aryl and Alkylethynylsilanes: A Stereo and Regioselective Route to Functionalized 2,2-Disubstituted Vinylsilanes," *Tetrahedron Letters*, 1986, pp. 6397-6400, vol. 27, No. 52.
Corriu, R. et al., "Uses of Si-N Bonds in Organic Synthesis. A Direct Synthesis of Functional Protected Propargylic Primary Amines," *Tetrahedron Letters*, 1984, pp. 1887-1890, vol. 25, No. 18.
Macinnes, I. et al., "Electron Delocalisation and Stabilisation in Substituted Amino- and Hydroxy-propynyl Radicals," *J. Chem, Soc. Perkin Trans. II*, 1987, pp. 1077-1082.
Andreev, A. et al., "Direct Electrophilic Silylation of Terminal Alkynes," *Organic Letters*, 2004, pp. 421-424, vol. 6, No. 3.
Jiang, H. et al., "Silylation of 1-alkynes with chlorosilanes promoted by Zn(OTf)$_2$: an efficient way to the preparation of alkynylsilanes," *Tetrahedron Letters*, 2005, pp. 517-519, vol. 46.
Rahaim, R. et al., "Zinc-Catalyzed Silylation of Terminal Alkynes," *J. Org. Chem.*, 2008, pp. 2912-2915, vol. 73.
Ostendorf, D. et al., "Silicon Compounds with Strong Intramolecular Steric Interactions, 71[1]," *Eur. J. Inorg. Chem.*, 1999, pp. 2301-2307.
Yang, L-M. et al., "Kumada-Corriu Reaction of Alkyl Halides with Alkynyl Nucleophiles," *Organic Letters*, 2004, pp. 1461-1463, vol. 6, No. 9.
Takahashi, S. et al., "A Convenient Synthesis of Ethynylarenes and Di-ethynylarenes," *Synthesis*, Aug. 1980; pp. 627-630.
Marciniec, B. et al., "Transformations of (Organo)silicon Compounds Catalyzed by Iridium Complexes," *Iridium Complexes in Organic Synthesis*, 2009, pp. 345-367.
Wang, J. et al., "Unique σ-Bond Metathesis of Silylalkynes Promoted by an *ansa*-Dimethylsilyl and Oxo-Bridged Uranium Metallocene," *J. Am. Chem. Soc.*, 2006, pp. 9350-9351, vol. 128.
Amemiya, R. et al., "GaCl$_3$ in Organic Synthesis," *Eur. J. Org. Chem.*, 2005, pp. 5145-5150.

(Continued)

*Primary Examiner* — Porfirio Nazario Gonzalez
*Assistant Examiner* — Kofi Adzamli
(74) *Attorney, Agent, or Firm* — Oliff PLC

(57) ABSTRACT

The present invention relates to new (triorganosilyl)alkynes and their derivatives having general formula 1 R$^1$—C≡C—Z (I) In its second aspect, this invention relates to a new selective method for the preparation of new and conventional (triorganosilyl)alkynes and their derivatives having the general formula 1, by the silylative coupling of terminal alkynes with halogenotriorganosilanes in the presence of an iridium catalyst and a tertiary amine.

7 Claims, No Drawings

(56) References Cited

OTHER PUBLICATIONS

Fischer, C. et al., "Direct Addition of TMS-acetylene to Aldimines Catalyzed by a Simple, Commercially Available Ir(I) Complex," *Organic Letters*, 2001, pp. 4319-4321, vol. 3, No. 26.

Tomioka, H. et al., "Photolysis of regioisomeric diazides of 1,2-diphenylacetylenes studied by matrix-isolation spectroscopy and DFT calculations," *Org. Biomol. Chem.*, 2003, pp. 4441-4450, vol. 1.

Allen, A. et al., "Preparation and crystal structure of a stable and persistent twisted tetraketene," *Chem. Commun.*, 1996, pp. 2171-2172.

Komarov, N.V., "Acetylene siloxanes in organomagnesium synthesis," *Izvestiya Akademii Nauk SSSR*, 1972, pp. 698-699, vol. 3 (Abstract only).

Kownacki, I. et al., "Silylative Coupling of Terminal Alkynes with Iodosilanes: New Catalytic Activation of sp-Hybridized Carbon-Hydrogen Bonds," *Organometallics*, 2011, pp. 2539-2545, vol. 30.

Shimizu, R. et al., "Dehydrogenative silylation of terminal alkynes by iridium catalyst," *Tetrahedron Letters*, 2000, pp. 907-910, vol. 41.

International Search Report issued in International Application No. PCT/PL2011/050056 on Jul. 27, 2012.

\* cited by examiner

(TRIORGANOSILYL)ALKYNES AND THEIR DERIVATIVES AND A NEW CATALYTIC METHOD FOR OBTAINING NEW AND CONVENTIONAL SUBSTITUTED (TRIORGANOSILYL)ALKYNES AND THEIR DERIVATIVES

The present invention relates to new (triorganosilyl) alkynes and their derivatives and a new selective method for obtaining new and conventional (triorganosilyl)alkynes and their derivatives by the silylative coupling of terminal alkynes with halogenotriorganosilanes.

Known methods for the synthesis of substituted triorganosilylalkynes may be divided in two groups: non-catalytic reactions, and processes catalyzed with transition metal complexes.

The former comprises mainly stoichiometric reactions between halogenotriorganosilanes and organolithium or organomagnesium compounds. The obtaining of functionalized, substituted triorganosilylalkynes based on stoichiometric reactions of halogenosilanes with alkinyloorganic compounds of lithium or magnesium enables the synthesis of a wide range of this type of compounds (1).

An organosilyl substituent may be introduced also with the use of lithium triorganosilylacetylide ($Li^{30}$ $^-C\equiv CSiR_3$) in a reaction with suitable alkyl-aryl ketones, leading to functionalized substituted triorganosilylalkynes (2).

Alternatively, Arcadi (3) disclosed a method for the synthesis of 1-N,N-bis(trimethyl-silyl)amino-3-trimethylsilyloprop-2-yne by reacting lithium N,N-bis(trimethylsilylamino)-propynyl with chlorotrimethylsilane.

Corriu (4) described a method to obtain 1-N,N-bis(trimethylsilyl)amino-3-trimethylsilylprop-2-yne by reacting (3-bromoprop-1-yne-1-yl)trimethylsilane with lithium N,N-bis(trimethylsilyl)amide.

Both methods require the use of strongly reactive organometallic reagents (Li, Mg), which are very expensive or are unstable and must be synthesized just before carrying out the reaction concerned, which makes it difficult to obtain the intended substituted triorganosilylalkynes, especially in a larger scale. The high reactivity of the organometallic derivatives of these metals results in the formation of a large quantity of undesirable reaction products, lowering the yield of the main product (silylalkyne), and making it difficult to isolate such product from the resulting reaction mixture.

Another known method to obtain aminofunctional ethynylsilanes, as disclosed by MacInnnes (5), is a reaction between chlorotrimethylsilane, propargyl bromide, and hexamethyldisilazane, initiated by organic peroxides (5). The use of explosive organic peroxides as initiators of radical reactions is very troublesome: special precautions in carrying out the process and monitoring the course of the process are required.

Another group of methods enabling the synthesis of substituted triorganosilylalkynes are reactions of direct silylation of terminal alkynes in the presence of stoichiometric amounts of zinc salts ($ZnCl_2$, $Zn(OSO_2CF_3)_2$). This group comprises the silylation of terminal alkynes with the use of silylamines (6), chlorosilanes (7), as well as trimethylsilyl trifluoromethylsulfonate ($F_3CS(O)_2OSiMe_3$) (8). Although such methods are characterized by good yields and selectivities, they require the use of zinc salts as intermediate reacting substances in at least equimolar amounts relative to the terminal alkyne, as well as very high, even 10-fold, stoichiometric excess of silylating reagents. In the case of chlorosilanes or $F_3CS(O)_2OSiMe_3$ it is also necessary to use tertiary amines which bind the trifluoromethylsulfonic acid or hydrogen halide being formed during the reaction.

A method is known to synthesize bissilyl-functionalized dialkynes by way of a photochemical reaction of a suitable silylene precursor (such as 1,1-ditertbutylsila-2,3-dimethylcyclopropane) with 1,4-substituted-1,3-butadiyne (9). However, the method is characterized by a very low yield, not exceeding 52%. Ditertbutylsilylene, which is formed during the reaction is an explosive compound, which limits any chances of the commercial use of the method.

Substituted triorganosilylalkynes are obtained in reactions, which are catalyzed by transition metal complexes or salts. An example of a reaction, catalyzed by transition metal complexes, to obtain substituted triorganosilylalkynes, is a coupling reaction between triorganosilylethynyl lithium or -magnesium with alkyl halides (10) or ethynyltriorganosilane with alkenyl or aryl halides in the presence of palladium complexes (11). The methods are characterized by highly variable selectivity which is up to 80%, depending on the type of reacting substances and catalysts used. Proper reaction products are also accompanied by numerous by-products, including dimers of the starting alkynes, which makes it difficult to isolate and purify silylalkynes from the post-reaction mixture.

Those skilled in the art are familiar with methods to obtain triorganosilylalkynes in reactions between terminal alkynes and triorganosubstituted silanes, catalyzed by iridium complexes (12). Such methods are based on dehydrogenative silylation reaction, which produces a triorganosilyl-functionalized alkyne and a number of by-products. If known iridium catalysts are used, the desirable product is obtained with a yield of not more than 40% because other, competing reactions are taking place at the same time. However, the compositions of the resulting post-reaction mixtures are so complex that the method is hardly of any practical use.

Disclosed in the Patent Application WO 2008020774 is a method for the synthesis of substituted triorganosilylalkynes by the silylating coupling of vinyl-substituted compounds of silicon and terminal alkynes in the presence of ruthenium(II) complexes. The process proceeds with good and high yields, although the desirable products may be accompanied by products of homocoupling of vinyl-substituted organosilicon compounds, affecting the process selectivity.

Also known in the art is a method to synthesize triorganosilylsubstituted alkynes in the process of cross-metathesis of 1,2-bis(trimethylsilyl)ethyne with terminal alkynes in the presence of a uranium complex (13). In this case as well, the principal process is accompanied by a number of side reactions, which reduce the yield of triorganosilylsubstituted alkynes, and hinder the operations involved in their isolation and purification; this reduces the final process efficiency.

Functionalized triorganosilylalkynes are also obtained by alkynylation of silylenolates by means of chloroethynyl silane in the presence of gallium(III) chloride (14) or by reacting aldimines with ethynyltrimethylsilane, catalyzed by iridium(I) complexes (15). Although such processes are characterized by high yields and product selectivities, they require the use of specific substrates in the form of aldimines, or unstable substituted chloroethynyl silanes, which limits the applicability of the method to the synthesis of only selected triorganosilyl-functionalized alkynes.

Those skilled in the art are also familiar with the method, as described by Arcadi (3), for the catalytic synthesis of substituted 1-(aminoaryl)-2-(triorganosilyl)alkynes in a reaction between ethynyltriorganosilanes and haloarylamines in the presence of the complex [$Pd(O(O)CCH_3)_2(PPh_3)_2$] and triethylamine, which produces respective 1-($H_2N$-arylo)-2-(triorganosilyl)ethynes. Such compounds are an intermediate product in the synthesis of 1-(N,N-bis(triorganosilylamino)aryl)-2-(triorganosilyl)ethynes, because only in the second step it is necessary to carry out the reaction substituting the hydrogen atoms in the amine group —NH$_2$ with triorganosilyl substitutes. The method has the important drawback of the necessity to use very specific haloarylamines.

Tomioka (16) described the method of coupling ethynyltriorganosilanes with respective halo-nitroaryl derivatives in the presence of the complex [PdCl$_2$(PPh$_3$)$_2$] and triethylamines whereby respective 1-(O$_2$N-arylo)-2-(triorganosilyl)ethynes are obtained.

Such compounds are an intermediate in the synthesis of 1-(N,N-bis(triorgano-silylamino)aryl)-2-(triorganosilyl)ethynes, because only the following steps comprise the reduction of the nitro group (—NO$_2$) to the amine group —(NH$_2$), followed by the substitution of hydrogen atoms in the amine group —NH$_2$ with triorganosilyl substitutes.

It was the purpose of this invention to provide new (triorganosilyl)alkynes and their derivatives and a new method for obtaining new and conventional (triorganosilyl)alkynes and their derivatives.

The invention relates to new (triorganosilyl)alkynes, having the general formula 1,

  (1)

in which
R$^1$ denotes —SiR$^2$R$^3$R$^4$ where R$^2$R$^3$R$^4$ are equal and denote a C$_{1-5}$ alkyl group or phenyl and
Z denotes 3-N,N-bis(trimethylsilylamino)phenyl, 4-N,N-bis(trimethylsilylamino)phenyl.

In its second aspect, this invention relates to a method to obtain (triorganosilyl)alkynes and their derivatives, having the general formula 1

  (1)

in which
R$^1$ denotes —SiR$^2$R$^3$R$^4$ where R$^2$R$^3$R$^4$ are equal and denote a C$_{1-5}$ alkyl group or phenyl and
Z denotes 3-N,N-bis(trimethylsilylamino)phenyl, 4-N,N-bis(trimethylsilylamino)phenyl, a group having the general formula 2

  (2)

in which E denotes phenylene or a group having the general formula 3

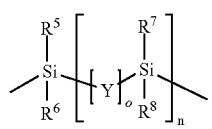  (3)

where
R$^5$, R$^6$, R$^7$, R$^8$ denote a C$_{1-5}$ alkyl group, phenyl group
o takes the value 1
n takes the value 0 or 1
Y denotes O or the group —CH$_2$—CH$_2$—
so that:
  if n denotes 0, then R$^5$ and R$^6$ are equal to each other or different,
  if n=1 then R$^5$, R$^6$, R$^7$ and R$^8$ are equal to one another.

Unexpectedly, it was discovered that some iridium(I) complexes having the general formula 4 form, in the presence of a tertiary amine having the general formula 5, an amine complex having the general formula 6 which catalyzes the selective reaction of silylative coupling of terminal alkynes with halogenosilanes, which produces (triorganosilyl)alkynes or their derivatives.

The catalyst used is an iridium complex having the general formula 4,

  (4)

in which L denotes (CO)$_2$ or cis,cis-1,5-cyclooctadiene (cod), and a tertiary amine having the general formula 5

  (5)

in which A$^1$A$^2$A$^3$ are equal or different and denote a C$_{1-5}$ alkyl, a C$_{5-7}$ cycloalkyl, an aryl, an arylalkyl, where the alkyl chain contains C$_{1-4}$, an alkylaryl where the alkyl chain contains C$_{1-4}$, so that none of the substitutes is a heteroaryl or a heteroaryl derivative.

The iridium complex forms, with the amine which functions as co-catalyst, a complex having the general formula 6

  (6)

in which L, A$^1$A$^2$A$^3$ denote the same as stated above and this complex only shows catalytic properties in the method of the invention.

The catalyst, of which the structure has changed as the result of combination with the amine, catalyzes the selective reaction of silylative coupling of terminal alkynes with halogenosilanes, producing (triorganosilyl)alkynes and their derivatives.

Preferably, the catalyst used is the complex [{Ir(μ-Cl)(CO)$_2$}$_2$].

The amine complex may be formed both in the reaction between a terminal alkyne and a halogenosilane, or may be introduced thereto as a final amine complex. In the former case, the amine and the iridium complex are added to the reaction medium and the amine complex is obtained in the course of mixing; in the latter, the amine and the iridium complex are dissolved in a solvent and mixed until the dissolution of the starting iridium complex, which functions as a pre-catalyst, and the formation with the tertiary amine of the proper catalyst which is introduced in a suitable ratio to the proper reaction medium.

In the method of the invention, the iridium complex is used in an amount in the range from 0.01 to 4 mol % relative to the functional terminal ethynyl group.

The amine having the formula 5 is used with an at least 2.2-fold excess relative to the iridium ion in the complex used plus an at least stoichiometric amount relative to the hydrogen halide formed in the reaction between the terminal alkyne and halogenosilanes.

The tertiary amine used in the method of the invention has a double role: on the one hand, it functions as a co-catalyst which, after being combined with the complex having the general formula 4, will change its structure and lead to the formation of a complex having the general formula 6; on the other, its excess binds the hydrogen halide which is formed in the reaction.

In its first embodiment, the method of the invention to obtain new and conventional (triorganosilyl)alkynes having the general formula 1, in which $R^1$ denotes —$SiR^2R^3R^4$
  where $R^2R^3R^4$ are equal or different and denote
    a $C_{1-5}$ alkyl,
    a phenyl, an aryl containing from 1 to 5 alkyl substitutes containing $C_{1-4}$,
    a siloxy group having the formula 7, $$—O—Si\begin{subarray}{l}R^9\\R^9\\R^9\end{subarray} \tag{7}$$

in which $R^9$ are equal or different and denote a $C^{1-3}$ alkyl, an aryl, or alkylaryl, containing from 1 to 5 $C_{1-4}$ alkyl substitutes so that none of the $R^2R^3R^4$ substitutes has a heteroaryl or a heteroaryl derivative,
Z denotes a group having the formula 2 in which $R^1$ denotes the same as stated above
E denotes phenylene or a group having the formula 3, in which:
  $R^5$, $R^6$, $R^7$, $R^8$ denote a $C_{1-5}$ alkyl group, a phenyl group, a siloxy group having the general formula 7, in which $R^9$ denotes the same as stated above,
  n takes the value 0 or 50
  o takes the value 0 or 1
  Y denotes O, the group $(CH_2)_m$ where m=1-16, $NR^{10}$, where the group $R^{10}$ denotes H, a $C_{1-5}$ alkyl, an aryl containing from 1 to 5 $C_{1-\alpha}$alkyl substitutes or alkoxy substitutes having $C_{1-4}$ alkyl radicals, an arylalkyl where the alkyl chain contains $C_{1-4}$, a silyl group having the general formula 8, $$—Si\begin{subarray}{l}R^{11}\\R^{11}\\R^{11}\end{subarray} \tag{8}$$

in which the substitutes $R^{11}$ are equal or different and denote a $C_{1-3}$ alkyl, an aryl containing from 1 to 5 alkyl substitutes containing $C_{1-4}$, a siloxy group having the general formula 7, where $R^9$ denotes the same as stated above except that the group $R^{10}$ is not a heteroaryl or a heteroaryl derivative,
so that:
  if n=0, then $R^4$ and $R^5$ are equal to each other or different,
  if n=1 and o=1 and Y denotes $(CH_2)_m$ or O or $NR^{10}$, then $R^5$, $R^6$, $R^7$ and $R^8$ are equal to one another; or the pairs $R^5$ and $R^7$, $R^6$ and $R^8$, $R^5$ and $R^6$, $R^7$ and $R^8$ are equal to one another but different from another pair,
  if n=1 and o=0, then it is possible that $R^5$, $R^6$, $R^7$ and $R^8$ are equal to one another; or the pairs $R^5$ and $R^7$, $R^6$ and $R^8$ are equal but different from the other pair,
  if Y is O and n=2-50, then $R^4$, $R^5$, $R^6$ and $R^7$ are equal to one another,
consists in reacting a suitable terminal alkyne having the general formula 9, in which $$H—C≡C—Z \tag{9}$$

Z denotes the same as stated above, and a suitable halogenotriorganosilane having the general formula 10, in which $$X—R^1 \tag{10}$$

X denotes Cl, Br, I, particularly iodine,
  $R^1$ denotes the same as stated above,
in the presence of an iridium catalyst having the formula 4 and a tertiary amine having the general formula 5.

The iridium catalyst used is an iridium complex having the general formula 4, preferably $[\{Ir(\mu\text{-}Cl)(CO)_2\}_2]$.

The catalyst is used in an amount in the range from 0.01 to 4 mol % relative to the functional terminal alkyne group, preferably in an amount in the range 1-2 mol %.

In its second embodiment, the method of the invention to obtain new and conventional (triorganosilyl)alkynes having the general formula 1, in which
  $R^1$ denotes —$SiR^2R^3R^4$
    where $R^2R^3R^4$ are equal or different and denote
      a $C_{1-5}$ alkyl, a $C_{5-7}$ cycloalkyl,
      a phenyl, an aryl containing from 1 to 5 alkyl substitutes containing $C_{1-4}$,
      a siloxy group having the formula 7, $$—O—Si\begin{subarray}{l}R^9\\R^9\\R^9\end{subarray} \tag{7}$$

in which $R^9$ are equal or different and denote a $C_{1-3}$ alkyl, an aryl, or an alkylaryl, containing from 1 to 5 alkyl substitutes containing $C_{1-4}$,
  so that none of the $R^2R^3R^4$ substitutes has a heteroaryl or a heteroaryl derivative,
Z denotes:
  a silyl group having the general formula 8 in which $R^{11}$ denotes the same as stated above, a siloxy group having the general formula 7 in which $R^9$ denotes the same as stated above
  a ferrocenyl group,
  a $C_{1-5}$ alkyl,
  a $C_{5-7}$ cycloalkyl,
  —$CH2NR^1_2$ in which $R^1$ denotes the same as stated above
  an arene with the fused aromatic ring number in the range from 2 to 6,
  a group having the general formula 11, $$-(R^{12})_y-\left(\begin{array}{c}R^{13}R^{14}R^{15}R^{16}\\ \\R^{13}R^{14}R^{15}R^{16}\end{array}\right)_w\left(R^{13}R^{14}R^{15}R^{16}R^{17}\right) \tag{11}$$

in which:
  y takes the values 0 or 1, and w takes the values from 0 to 2
  $R^{12}$ denotes a $C_{1-5}$ alkylene group, a $C_{5-7}$ cycloalkylene group,
  $R^{13}$, $R^{14}$, $R^{15}$, $R^{16}$, $R^{17}$ are equal or different and denote a hydrogen atom, a $C_{1-4}$ alkyl chain, a halogen, an alkoxy group where the alkyl radical contains $C_{1-3}$, —$NH_2$, —OH, —$OR^1$ or $NR^1_2$ in which $R^1$ denotes the same as stated above, so that when:

in the general formula 11, w=1 and y=1, then $R^{13}$, $R^{14}$, $R^{15}$, $R^{16}$, $R^{17}$ are equal or different and denote a hydrogen atom, a $C_{1-4}$ alkyl chain, a halogen, an alkoxy group in which the alkyl radical contains $C_{1-3}$, in the general formula, y=0 and w takes a value in the range from 0 to 2, then $R^{13}$, $R^{14}$, $R^{15}$, $R^{16}$, $R^{17}$ denote the same as stated above and, moreover, at least one of the substituents $R^{13}$, $R^{14}$, $R^{15}$, $R^{16}$, $R^{17}$ denotes phenyl, aryl with the exception of heteroaryls, —$NH^2$, —OH, —$OR^1$ or $NR^1_2$, in which $R^1$ denotes the same as stated above consists in reacting a suitable terminal alkyne having the general formula 9 in which Z denotes the same as stated above and a suitable halogenotriorganosilane having the general formula 10 in which X denotes Cl, Br, I, particularly iodine, and $R^1$ denotes the same as stated above, in the presence of an iridium catalyst having the formula 4 and a tertiary amine having the general formula 5.

The iridium catalyst used is an iridium complex having the general formula 4, preferably [{Ir(μ-Cl)(CO)$_2$}$_2$].

The catalyst is used in an amount in the range from 0.01 to 4 mole % relative to the functional terminal alkyne group, preferably in an amount in the range 0.5-1 mole %. In the synthesis of the compounds containing amine substitutes, the catalyst, preferably, is used in an amount in the range from 0.5 to 2 mole %.

In all the embodiments of the invention, a tertiary amine having the general formula 5 is introduced, in a solvent at ambient temperature and with vigorous mixing, to an iridium complex, having the general formula 4, in the form of suspension, and mixing is continued until the iridium complex is dissolved.

A suitable terminal alkyne and a triorganohalogenosilane are introduced one after another to the resulting system at a room temperature and the resulting reaction mixture is heated to a temperature above 60° C. but not higher than 140° C. until the reaction is completed, i.e., until the complete conversion of the starting terminal alkyne, whereupon raw product is isolated and purified.

The reaction is carried out under inert gas in a solvent selected from the group comprising aromatic organic compounds, most preferably in toluene.

The reaction runs at any selected ratio of the reacting substances, however, unfavourable ratios lead to the formation of a number of by-products. If the halogenotriorganosilane is used at equimolar amounts relative to a single alkyne group in the terminal alkyne, the process selectivity will not reach its achievable maximum value because the products of a number of competitive reactions, i.e., trimerization and oligomerization of the starting terminal alkyne, are formed in addition to the desirable product. If the system comprises an at least 0.1-fold stoichiometric excess of the halogenotriorganosilane and the tertiary amine relative to a single alkyne group, then selectivity is shifted towards the proper product having the general formula 1 by a more efficient binding of hydrogen halide in the form of a suitable hydrogen ammonium salt [HNA$^1$A$^2$A$^3$]X, which results in effect in increased process selectivity. According to the invention, the reaction is preferably carried out at a 0.4-0.7-fold molar excess of the halogenotriorganosilane and 0.5-0.8-fold molar excess of the tertiary amine relative to a single functional alkyne group. According to the invention, the reaction is carried out at a temperature in the range from 60-140° C., most preferably at 80° C. Generally, the reaction time is 24 hrs.

According to the method of the invention, the synthesis is carried out under inert gas, most preferably argon, in a reactor, which is protected from moisture. All liquid reacting substances and the solvent ought to be dehydrated and deoxidized because of the sensitivity and possible decomposition of the catalyst and the starting halogenosilane in the presence of trace amounts of water and oxygen. The reaction mixture is then heated and mixed until the reaction is complete.

Reversing the sequence in which the reacting substances are added, i.e., first the halogenotriorganosilane, second the alkyne, and third the tertiary amine, is also possible although this may lead to reduced process selectivity or a completely blocked activity of the iridium catalytic system.

Raw product is isolated and purified by known methods. Generally, isolation consists in evaporation of the solvent from the post-reaction mixture, followed by separation of the raw product from the catalyst and hydrogen triorganoammonium halide, which is formed as a by-product, on a silica gel-packed chromatographic column, using aliphatic hydrocarbons, preferably hexane or pentane, as eluent.

In contrast to previously known, prior-art methods, synthesis according to the method of the invention is a method of which the selectivity reaches 98%, in which the catalyst is used in small amounts and a much smaller stoichiometric excess of the halogenotriorganosilane and the tertiary amine, compared to the known method, described by Jiang.

The compounds obtained by the method of the invention are useful as substrates, enabling the synthesis of molecular and macromolecular compounds with a high πconjugated multiple-bond systems with precisely dedicated chemical, electronic, and optoelectronic properties for use in the manufacturing of electronic luminescent, photoluminescent elements, or photosensors.

The subject of the present invention is illustrated by means of examples, which are intended to illustrate rather than limit the scope of the invention.

Products are identified based on the results of:

spectral analysis of $^1$H, $^{13}$C and $^{29}$Si NMR, which have been recorded using the spectrometers Brucker Ultra Shield 600 MHz and Varian Mercury VT 400 MHz.

elemental analysis, performed using Vario EL Elemental apparatus.

Shown in Table 1 are data obtained by elementary analysis and NMR.

EXAMPLE 1

A reactor with a capacity of 40 mL, equipped with a magnetic stirrer was filled, under argon atmosphere, with 0.0085 g (0.015 mmol) of [{Ir(μ-Cl)(CO)$_2$}$_2$], and then with 8 mL of anhydrous and deoxidized toluene and 0.7 g (5.4 mmol) of NEt(i-Pr)$_2$. The whole mixture was stirred until the starting iridium(I) complex was dissolved, and then 0.306 g (3mmol) of phenylacetylene and 0.96 g (4.8 mmol) of ISiMe$_3$ were added to the resulting mixture. The reaction was carried out at a temperature of 80° C. until complete conversion of phenylacetylene. After the reaction was completed, the solvent was evaporated at a reduced pressure along with any residual unreacted substrates in order to remove the catalyst from the reaction mixture and then the residue was transferred onto a chromatographic column packed with silica gel and product was isolated using hexane as eluent. The solvent was initially evaporated from the eluate, and the residual product was distilled by means of the "trap-to-trap" technique at a reduced pressure to obtain 0.47 g of phenylethynyltrimethylsilane, with a yield of 90%.

EXAMPLE 2

Following the procedure used in Example 1, a reaction was carried out between:
    0.475 g (3 mmol) 4-t-Bu-phenylacetylene
    0.96 g (4.8 mmol) of $ISiMe_3$
    in the presence of
    0.0085 g (0.015 mmol) of the complex $[\{Ir(\mu-Cl)(CO)_2\}_2]$
    0.70 g (5.4 mmol) of $NEt(i-Pr)_2$
The product was 0.59 g of 1-(4-t-Bu-phenyl)-2-trimethylsilylethyne, obtained with a yield of 85%.

EXAMPLE 3

Following the procedure used in Example 1, a reaction was carried out between:
    0.511 g (3 mmol) of $HC\equiv CC(Me)(Et)(OSiMe_3)$
    0.96 g (4.8 mmol) of $ISiMe_3$
    in the presence of:
    0.017 g (0.03 mmol) of the complex $[\{Ir(\mu-Cl)(CO)_2\}_2]$
    0.70 g (5.4 mmol) of $NEt(i-Pr)_2$
The product was 0.68 g of 1-trimethylsilyl-3-methyl-3-trimethylsiloxy-1-butyne, obtained with a yield of 94%.

EXAMPLE 4

Following the procedure used in Example 1, a reaction was carried out between:
    0.393 g (2 mmol) of 1-ethynyl-1-trimethylsiloxy-cyclohexane
    0.64 g (3.2 mmol) of $ISiMe_3$
    in the presence of:
    0.0113 g (0.02 mmol) of the complex $[\{Ir(\mu-Cl)(CO)_2\}_2]$
    0.47 g (3.6 mmol) of $NEt(i-Pr)_2$
    The product was 0.51 g of 1-trimethyisilylethynyl-1-trimethylsiloxy-cyclohexane, obtained with a yield of 95%.

EXAMPLE 5

A reactor with a capacity of 30 mL, equipped with a magnetic stirrer, was filled under argon atmosphere with 0.0113 g (0.02 mmol) of the complex $[\{Ir(\mu-Cl)(CO)_2\}_2]$, 10 mL of toluene and 0.827 g (6.4 mmol) of $NEt(i-Pr)_2$. The whole mixture was stirred until the starting iridium(I) complex was dissolved, and then 0.248 g (2 mmol) of 1-ethynyl-1-hydroxy-cyclohexane was added. In the following step, 1.200 g (6 mmol) of $ISiMe_3$ was added slowly at a room temperature, whereafter the mixture was heated to 80° C. while stirring vigorously. The reaction was continued until complete conversion of the starting alkyne. After the reaction was completed the solvent was evaporated at a reduced pressure along with any unreacted substrates, The silylation product was isolated by means of pentane, using a cannula system. The solvent was initially evaporated from the extract, and then a raw product was purified on a $SiO_2$-packed column (modified with a 15% hexane solution of $Et_3N$), using hexane as eluent. The product was 0.52 g of 1-trimethylsilylethynyl-1-trimethylsiloxy-cyclohexane, obtained with a yield of 91%.

EXAMPLE 6

Following the procedure used in Example 1, a reaction was carried out between:
    0.561 g (2 mmol) of 3,3-diphenyl-3-trimethylsiloxy-1-propyne
    0.64 g (3.2 mmol) of $ISiMe_3$
    in the presence of:
    0.0113 g (0.02 mmol) of the complex $[\{Ir(\mu-Cl)(CO)_2\}_2]$
    0.47 g (3.6 mmol) of $NEt(i-Pr)_2$
The product was 0.67 g of 1-trimethylsilyl-3,3-diphenyl-3-trimethylsiloxy-1-propyne, obtained with a yield of 95%.

EXAMPLE 7

Following the procedure used in Example 1, a reaction was carried out between:
    0.42 g (2 mmol) of ethynylferrocene
    0.64 g (3.2 mmol) of $ISiMe_3$
    in the presence of:
    0.0113 g (0.02 mmol) of the complex $[\{Ir(\mu-Cl)(CO)_2\}_2]$
    0.47 g (3.6 mmol) of $NEt(i-Pr)_2$
The product was 0.51 g of 1-ferrocenyl-2-trimethylsilylethyne, obtained with a yield of 90%.

EXAMPLE 8

Following the procedure used in Example 1, a reaction was carried out between:
    0.363 g (2 mmol) of $HC\equiv CSi(iPr)_3$
    0.64 g (3.2 mmol) of $ISiMe_3$
    in the presence of:
    0.0113 g (0.02 mmol) of the complex $[\{Ir(\mu-Cl)(CO)_2\}_2]$
    0.47 g (3.6 mmol) of $NEt(i-Pr)_2$
The product was 0.49 g of 1-(tri-iso-propylsilyl)-2-trimethylsilylethyne, obtained with a yield of 97%.

EXAMPLE 9

Following the procedure used in Example 1, a reaction was carried out between:
    0.32 g (2 mmol) of $HC\equiv SiMe_2Ph$
    0.64 g (3.2 mmol) of $ISiMe_3$
    in the presence of:
    0.0113 g (0.02 mmol) of the complex $[\{Ir(\mu-Cl)(CO)_2\}_2]$
    0.47 g (3.6 mmol) of $NEt(i-Pr)_2$
The product was 0.44 g of 1-dimethylphenylsilyl-2-trimethylsilylethyne, obtained with a yield of 95%.

EXAMPLE 10

A reactor with a capacity of 25 mL, equipped with a magnetic stirrer was filled, under argon atmosphere, with 0.017 g (0.03 mmol) of $[\{Ir(\mu-Cl)(CO)_2\}_2]$, and then with 10 mL of anhydrous and deoxidized toluene and 0.7 g (5.4 mmol) of $NEt(i-Pr)_2$. The whole mixture was stirred until the starting iridium(I) complex was dissolved completely, and then 0.274 g (1.5mmol) of 1,3-diethynyltetramethyldisiloxane and 1.02 g (5.1 mmol) of $ISiMe_3$ were added to the resulting mixture. The reaction was carried out at a temperature of 80° C. until complete conversion of 1.3-diethynyltetramethyldisiloxane. After the reaction was completed, in order to remove the catalyst from the reaction mixture, the solvent was evaporated along with any residual unreacted substrates, and then the residue was transferred onto a chromatographic column packed with silica gel and the product was isolated using hexane as eluent. The product was 0.45 g of 1,3-bis(trimethylsilylethynyl)-1,1,3,3-tetramethyldisiloxane, obtained with a yield of 92%.

EXAMPLE 11

Following the procedure used in Example 10, a reaction was carried out between:
- 0.292 g (1.5 mmol) of 1,2-bis(dimethylethynylsilyl)ethane
- 0.96 g (5.1 mmol) of ISiMe$_3$
- in the presence of
- 0.017 g (0.03 mmol) of the complex [{Ir($\mu$-Cl)(CO)$_2$}$_2$]
- 0.70 g (5.4 mmol) of NEt(i-Pr)$_2$ The product was 0.44 g of 1,2-(bis(trimethylsilylethynyl)dimethylsilyl)ethane, obtained with a yield of 86%

EXAMPLE 12

Following the procedure used in Example 10, a reaction was carried out between:
- 0.189 g (1.5 mmol) of 1,4-diethynylbenzene
- 1.02 g (5.1 mmol) of ISiMe$_3$
- in the presence of:
- 0.01.7 g (0.03 mmol) of the complex [{Ir($\mu$-Cl)(CO)$_2$}$_2$]
- 0.70 g (5.4 mmol) of NEt(i-Pr)$_2$ The product was 0.39 g of 1,4-bis(trimethylsilylethynyl)benzene, obtained with a yield of 97%.

EXAMPLE 13

Following the procedure used in Example 10, a reaction was carried out between:
- 0.255 g (1.5 mmol) of diethynylmethylphenylsilane
- 1.02 g (5.1 mmol) of ISiMe$_3$
- in the presence of:
- 0.017 g (0.03 mmol) of the complex [{Ir($\mu$-Cl)(CO)$_2$}$_2$]
- 0.70 g (5.4 mmol) of NEt(i-Pr)$_2$ The product was 0.43 g bis(trimethylsilylethynyl)phenylmethylsilane, obtained with a yield of 91%.

EXAMPLE 14

Following the procedure used in Example 10, a reaction was carried out between:
- 0.384 g (1.5 mmol) of diethynyldiphenylsilane
- 1.02 g (5.1 mmol) of ISiMe$_3$
- in the presence of:
- 0.017 g (0.03 mmol) of the complex [{Ir($\mu$Cl))(CO)$_2$}$_2$]
- 0.70 g (5.4 mmol) of NEt(i-Pr)$_2$ The product was 0.54 g bis(trimethylsilylethynyl)diphenylsilane, obtained with a yield of 96%.

EXAMPLE 15

A reactor with a capacity of 40 mL, equipped with a magnetic stirrer was filled, under argon atmosphere, with 0.0085 g (0.015 mmol) of [{Ir($\mu$-Cl)(CO)$_2$}$_2$], and then with 25 mL of anhydrous and deoxidized toluene and 0.7 g (5.4 mmol) of NEt(i-Pr)$_2$. The whole mixture was stirred until the starting iridium(I) complex was dissolved, and then 0.598 g (3 mmol) of (Me$_3$Si)$_2$NCH$_2$C≡CH and 0.96 g (4.8 mmol) of ISiMe$_3$ were added to the resulting mixture. The reaction was carried out at a temperature of 80° C. until complete conversion of (Me$_3$Si)$_2$NCH$_2$C≡CH. After the reaction was completed, in order to remove the catalyst from the reaction mixture the solvent was evaporated at a reduced pressure along with any residual unreacted substrates, and then anhydrous pentane was added to the residue. The resulting suspension was filtered and the resulting deposit was rinsed with two portions of a solvent. The solvent was initially evaporated from the filtrate, and the residual product was distilled by means of the "trap-to-trap" technique at a reduced pressure to obtain 1.45 g of 1-(N,N-bis(trimethyl-silyl)amino)-3-trimethylsilylprop-2-yne, obtained with a yield of 96%.

EXAMPLE 16

Following the procedure used in Example 15, a reaction was carried out between:
- 1.57 g (6 mmol) of 3-N,N-bis(trimethylsilylamino)phenylacetylene
- 1.92 g (9.6 mmol) of ISiMe$_3$
- in the presence of
- 0.034 g (0.06 mmol) of the complex [{Ir($\mu$-Cl)$_2$}$_2$]
- 1.40 g (10.8 mmol) of NEt(i-Pr)$_2$ The product was 1.9 g of 1-(3-N,N-bis(trimethylsilyl)aminophenyl)-2-trimethylsilylethyne, obtained with a yield of 95%.

EXAMPLE 17

Following the procedure used in Example 15, a reaction was carried out between:
- 1.57 g (6 mmol) of 3-N,N-bis(trimethylsilylamino)phenylacetylene
- 1.92 g (9.6 mmol) of ISiMe$_3$
- in the presence of
- 0.0403 g (0.06 mmol) of the complex [{Ir($\mu$-Cl)(cod)}$_2$]
- 1.40 g (10.8 mmol) of NEt(i-Pr)$_2$ The product was 1.9 g of 1-(3-N,N-bis(trimethylsilyl)aminophenyl)-2-trimethylsilylethyne, obtained with a yield of 78%.

EXAMPLE 18

A reactor with a capacity of 40 mL, equipped with a magnetic stirrer was filled, under argon atmosphere, with 0.0085 g (0.015 mmol) of [{Ir($\mu$-Cl)(CO)$_2$}$_2$], and then with 8 mL of anhydrous and deoxidized toluene and 0.7 g (5.4 mmol) of NEt(i-Pr)$_2$. The whole mixture was stirred until the starting iridium(I) complex was dissolved, and then 0.535 g (3 mmol) of 4-ethynylbiphenyl and 0.96 g (4.8 mmol) of ISiMe$_3$ were added to the resulting mixture. The reaction was carried out at a temperature of 80° C. until complete conversion of 4-ethynylbiphenyl. After the reaction was completed, in order to remove the catalyst from the reaction mixture the solvent was evaporated at a reduced pressure along with any residual unreacted substrates. The silylation product was extracted by means of pentane using a cannula system. The solvent was initially evaporated from the extract, and then raw product was purified on a SiO$_2$-packed column (modified with a 15% hexane solution of Et$_3$N), using hexane as eluent. The product was 0.706 g of 4-(trimethylsilylethynyl)biphenyl, obtained with a yield of 94%.

EXAMPLE 19

Following the procedure used in Example 18, a reaction was carried out between:
- 1.07 g (6 mmol) of 4-ethynylbiphenyl
- 1.92 g (9.6 mmol) of ISiMe$_3$
- in the presence of
- 0.017 g (0.03 mmol) of the complex [{Ir($\mu$-Cl)(CO)$_2$}$_2$]
- 1.40 g (10.8 mmol) of NEt(i-Pr)$_2$ The product was 1.44 g of 4-(trimethylsilylethynyl)biphenyl, obtained with a yield of 96%.

EXAMPLE 20

Following the procedure used in Example 18, a reaction was carried out between:
- 0.457 g (3 mmol) of 1-ethynylnaphthalene
- 0.96 g (4.8 mmol) of ISiMe$_3$
in the presence of:
- 0.0085 g (0.015 mmol) of the complex [{Ir(μ-CS)(CO)$_2$}$_2$]
- 0.70 g (5.4 mmol) of NEt(i-Pr)$_2$ The product was 0.639 g of 1-(trimethylsilylethynyl)naphthalene, obtained with a yield of 95%.

EXAMPLE 21

Following the procedure used in Example 18, a reaction was carried out between:
- 0.914 g (6 mmol) of 1-ethynylnaphthalene
- 1,92 g (9.6 mmol) of ISiMe$_3$
in the presence of:
- 0.017 g (0.03 mmol) of the complex [{Ir(μ-Cl)(CO)$_2$}$_2$]
- 1.4 g (10.8 mmol) of NEt(i-Pr)$_2$ The product was 1.305 g of 1-(trimethylsilylethynyl)naphthalene, obtained with a yield of 97%,

EXAMPLE 22

Following the procedure used in Example 18, a reaction was carried out between:
- 0.684 g (3 mmol) of 2-(4-ethynylphenyl)-4,4,5,5-tetramethyl-1,3,2-dioxoborate
- 0.96 g (4.8 mmol) of ISiMe$_3$
in the presence of:
- 0.017 g (0.03 mmol) of the complex [{Ir(μ-Cl)(CO)$_2$}$_2$]
- 0.70 g (5.4 mmol) of NEt(i-Pr)$_2$ The product was 0.807 g of 2-(4-trimethylsilylethynylphenyl)-4,4,5,5-tetramethyl-1,3,2-dioxoborate, obtained with a yield of 94%.

EXAMPLE 23

Following the procedure used in Example 18, a reaction was carried out between:
- 1.368 g of (6 mmol) of 2-(4-ethynylphenyl)-4,4,5,5-tetramethyl-1,3,2-dioxoborate
- 1.92 g of (9.6 mmol) of ISiMe$_3$
in the presence of:
- 0.034 g of (0.06 mmol) of the complex [{Ir(μ-Cl)(CO)$_2$}$_2$]
- 1.4 g of (10.8 mmol) of NEt(i-Pr)$_2$ The product was 1.649 g of 2-(4-trimethylsilylethynylphenyl)-4,4,5,5-tetramethyl-1,3,2-dioxoborate, obtained with a yield of 96%.

EXAMPLE 24

A reactor with a capacity of 40 mL, equipped with a magnetic stirrer was filled, under argon atmosphere, with 0.017 g (0.03 mmol) of [{Ir(μ-Cl)(CO)$_2$}$_2$], and then with 25 mL of anhydrous and deoxidized toluene and 0.7 g (5.4 mmol) of NEt(i-Pr)$_2$. The whole mixture was stirred until the starting iridium(I) complex was dissolved, and then 0.785 g (3 mmol) of 4-(Me$_3$Si)$_2$NC$_6$H$_4$C≡CH and 0.96 g (4.8 mmol) of ISiMe$_3$ were added to the resulting mixture. The reaction was carried out at a temperature of 80° C. until complete conversion of 4-(Me$_3$Si)$_2$NC$_6$H$_4$C≡CH. After the reaction was completed, in order to remove the catalyst from the reaction mixture the solvent was evaporated at a reduced pressure along with any residual unreacted substrates, and then anhydrous pentane was added to the residue. The resulting suspension was filtered and the resulting deposit was rinsed with two portions of a solvent. The solvent was initially evaporated from the filtrate, and the residual product was distilled by means of the "trap-to-trap" technique at a reduced pressure to obtain 0.941 g of 1-(4-N,N-bis(trimethyl-silyl)aminophenyl)-2-trimethylsilylethyne, obtained with a yield of 94%,

EXAMPLE 25

Following the procedure used in Example 18, a reaction was carried out between:
- 1.57 g (6 mmol) of 4-N,N-bis(trimethylsilylamino)phenylacetylene
- 1.92 g (9.6 mmol) of ISiMe$_3$
in the presence of
- 0.034 g (0.06 mmol) of the complex [{Ir(μ-Cl)(CO)$_2$}$_2$]
- 1.40 g (10.8 mmol) of NEt(i-Pr)$_2$ The product was 1.9 g of 1-(4-N,N-bis(trimethylsilyl)aminophenyl)-2-trimethylsilylethyne, obtained with a yield of 95%.

Literature
1. W. P. Weber, *Silicon Reagents for Organic Synthesis*, Springer-Veriag, Berlin, 1983, 129-158
2. M. Bolourtchian, R. Zadmard, M. R. Saidi, *Monatshefte füf Chemie* 1999,130, 333-336
3. A. Arcadi, S. Cacchi, F. Marinelli *Tetrahedron Lett*, 1986, 27, 6397-6400
4. R. J. P Corriu, Robert, V. Huynh, J. J. E. Moreau, *Tetrahedron Lett.*, 1984, 25, 1887-1890
5. I. MacInnes, Iain; J, C. Walton, *J. Chem. Soc., Perkin Transactions 2: Physical Organic Chemistry*, 1987, 1077-1082
6. A. A. Anreev, V. V. Konshin, N. V. Komarov, M. Rubin, Ch. Brouwer, V. Gevorgyan, V. *Org. Lett.* 2004, 6, 421-424
7. H. Jiang, S. Zhu, S. *Tetrahedron Lett.* 2005, 46, 517-519
8. R. J. Rahaim Jr., J. T. Shaw, *J. Org. Chem.* 2008, 73, 2912-2915
9. D. Osterdorf, L. Kirmaier, W. Saak, H. Marsmann, M. Weidenbruch, *Eur. J. Inorg. Chem.* 1999, 12, 2301-2307)
10. L.-M. Yang, L.-F. Huang, T.-Y. Luh, *Org. Lett.* 2004, 6, 1461-1463
11. S. Takahashi, Y. Kuroyama, K. Sonogashira, N. Hagihara, *Synthesis,* 1980
12. B. Marciniec, I. Kownacki Transformations of (organo) siliocon compounds catalyzed by iridium complexes in *Iridum Complexes in organic synthesis* (Luis A. Oro, Carmen Claver, eds.), Wiley-VCH Veriag GmbH & Co. KGaA, Weinheim, 2009, chapter 14, pp. 345-367
13. J. Wang, Y. Gurevich, M. Botoshansky, M. S. Eisen, *J. Am. Chem. Soc.* 2006, 128, 9350-9351
14. R. Amemiya, M. Yamaguchi, *Eur. J. Org. Chem.* 2005, 5145-5150
15. Ch. Fischer, E .M. Carreira, *Organic Letters,* 2001, 3, 4319-4321
16. H. Tomioka, S. Sawai, *Organic and Biomolecular Chemistry,* 2003, 1, 4441-4450

TABLE 1

Characterization of the compounds obtained in the Examples.

| Example | Name | Elemental analysis + NMR analysis |
|---------|------|-----------------------------------|
| 1 | phenylethynyltrimethylsilane | Analysis calculated for $C_{11}H_{14}Si$ C 75.79; H 8.10; found C 75.87; H 8.12; $^1$H NMR (300 MHz, $CDCl_3$, 300 K) δ (ppm) = 7.46 (m, 2H, o,p-Ph); 7.31 (m, 3H, o,p-Ph); 0.25 (s, 18H, —SiMe$_3$); $^{13}$C NMR (75.46 MHz, $C_6D_6$, 300 K) δ (ppm) = 131.95; 128.46; 128.18; 123.10 (Ph); 105.08 (Ph—C≡C—SiMe$_3$); 94.08 (Ph—C≡C—SiMe$_3$); −0.03 (SiMe$_3$); $^{29}$Si NMR (119.23 MHz, $C_6D_6$, 300 K) δ (ppm) = −17.74 (—SiMe$_3$). |
| 2 | 1-(4-t-Bu-phenyl)-2-trimethylsilylethyne | Analysis calculated for $C_{15}H_{22}Si$; C 78.19; H 9.62; found C 78.27; H 9.66; $^1$H NMR (300 MHz, $CDCl_3$, 300 K) δ (ppm) = 7.46 (m, 2H, m-Ph); 7.40 (d, 2H, —$C_6H_4$—); 7.31 (d, 2H, —$C_6H_4$—); 1.30 (s, 9H, —$CMe_3$); 0.24 (s, 9H, —SiMe$_3$); $^{13}$C NMR (74.46 MHz, $C_6D_6$, 300 K) δ (ppm) = 151.751; 131.67; 125.17; 120.08 (—$C_6H_4$—); 105.03 (C≡C—SiMe$_3$); 93.28 (C≡C—SiMe$_3$); 34.77 (CMe$_3$); 31.14 (—CMe$_3$); 0.03 (—SiMe$_3$); $^{29}$Si NMR (119.23 MHz, $C_6D_6$, 300 K) δ (ppm) = −17.96 (SiMe$_3$). |
| 3 | 1-trimethylsilyl-3-methyl-3-trimethylsilyloxy-1-butyne | Analysis calculated for $C_{12}H_{26}OSi_2$ C 59.43; H 10.81; found C 59.52; H 10.86; $^1$H NMR (300 MHz, $CDCl_3$, 300 K) δ (ppm) = 1.61 (m, 2H, —$CH_2$—); 1.41 (s, 3H, C—Me); 0.96 (t, 3H, $CH_2CH_3$) 0.18 (s, 9H, OSiMe$_3$); 0.16 (s, 9H, SiMe$_3$); $^{13}$C NMR (75.45 MHz, $C_6D_6$, 300 K) δ (ppm) = 109.96 (Me$_3$Si—C≡C—); 88.40 (Me$_3$Si—C≡C—); 70.13 (C—OSiMe$_3$); 38.06 (—CH$_2$—); 30.74 (Me); 8.99 (—CH$_2$CH$_3$) 1.90 (SiMe$_3$); 1.01 (OSiMe$_3$); $^{29}$Si NMR (119.23 MHz, $C_6D_6$, 300 K) δ (ppm) = 13.33 (OSiMe$_3$); −18.56 (SiMe$_3$). |
| 4i5 | 1-trimethylsilylethynyl-1-trimethylsiloxy-cyclohexane | Analysis calculated for $C_{14}H_{28}OSi_2$ C 62.62; H 10.51; found C 62.70; H 10.54; $^1$H NMR (300 MHz, $CDCl_3$, 300 K) δ (ppm) = 1.80; 1.51; 1.23 (m, 10H, $C_6H_{10}$); 0.18 (s, 9H, OSiMe$_3$); 0.17 (s, 9H, SiMe$_3$); $^{13}$C NMR (75.45 MHz, $C_6D_6$, 300 K) δ (ppm) = 110.09 (Si—C≡C—); 89.50 (Si—C≡C); 70.12 (C—OSiMe$_3$); 41.15; 25.28; 23.13 (Cy); 2.07 (SiMe$_3$); 1.01 (OSiMe$_3$); $^{29}$Si NMR (119.23 MHz, $C_6D_6$, 300 K) δ (ppm) = 13.07 (—OSiMe$_3$); −18.61 (SiMe$_3$). |
| 6 | 1-trimethylsilyl-3,3-diphenyl-3-trimethylsiloxy-1-propyne | Analysis calculated for $C_{21}H_{28}OSi_2$ C 71.53; H 8.00; found C 71.65; H 8.04; $^1$H NMR (300 MHz, $CDCl_3$, 300 K) δ (ppm) = 7.55 (m, 4H, m-Ph); 7.25 (m, 6H, o,p-Ph); 0.24 (s, 9H, OSiMe$_3$); 0.12 (s, 9H, SiMe$_3$); $^{13}$C NMR (75.45 MHz, $C_6D_6$, 300 K) δ (ppm) = 146.55; 127.90; 127.05; 125.93 (Ph); 108.05 (C≡C—SiMe$_3$); 92.92 (C≡C—SiMe$_3$); 75.75 (CPh$_2$(OSiMe$_3$)); 1.58 (OSiMe$_3$); −0.27 (SiMe$_3$); $^{29}$Si NMR (119.23 MHz, $C_6D_6$, 300 K) δ (ppm) = 17.41 (OSiMe$_3$); −17.60 (SiMe$_3$). |
| 7 | 1-ferrocenyl-2-trimethylsilylethyne | Analysis calculated for $C_{15}H_{18}FeSi$; C 63.83; H 6.43; found C 65.97; H 6.48; $^1$H NMR (300 MHz, $CDCl_3$, 300 K) δ (ppm) = 4.44 (m, 2H, Cp); 4.22 (m); 4.20 (s); 4.89 (m) (7H, Cp); 0.23 (s, 9H, SiMe$_3$); $^{13}$C NMR (75.45 MHz, $C_6D_6$, 300 K) δ (ppm) = 104.16 (C≡C—SiMe$_3$); 97.38 (Cp); 90.50 (C≡C—SiMe$_3$); 71.71; 70.11; 68.69 (Cp); 0.24 (SiMe$_3$); $^{29}$Si NMR (119.23 MHz, $C_6D_6$, 300 K) δ (ppm) = −18.50 (SiMe$_3$). |
| 8 | 1-(tri-iso-propylsilyl)-2-trimethylsilylethyne | Analysis calculated for $C_{14}H_{30}Si_2$ C 66.06; H 11.88; found C 66.14; H 11.91; $^1$H NMR (300 MHz, $CDCl_3$, 300 K) δ (ppm) = 1.05 (m, 21H, i-Pr); 0.17 (s, 9H, SiMe$_3$); $^{13}$C NMR (75.45 MHz, $C_6D_6$, 300 K) δ (ppm) = 116.73 (C≡C—Si(i-Pr)$_3$); 110.14 (C≡C—SiMe$_3$); 18.55 (Me); 11.06 (C—H); 0.02 (SiMe$_3$); $^{29}$Si NMR (119.23 MHz, $C_6D_6$, 300 K) δ (ppm) = −2.77 (Si(i-Pr)$_3$); −19.35 (SiMe$_3$). |
| 9 | 1-dimethylphenylsilyl-2-trimethylsilylethyne | Analysis calculated for $C_{13}H_{20}Si_2$ C 67.17; H 8.67; found C 67.29; H 8.70; $^1$H NMR (300 MHz, $CDCl_3$, 300 K) δ (ppm) = 7.64 (m, 2H, m-Ph); 7.38 (m, 3H, o,p-Ph); 0.41 (s, 6H, SiMe$_2$Ph); 0.20 (s, 9H, SiMe$_3$); $^{13}$C NMR (75.45 MHz, $C_6D_6$, 300 K) δ (ppm) = 136.93; 133.70; 129.35; 127.83 (—Ph); 116.03 (C≡C—SiMe$_3$); 111.36 (C≡C—SiMe$_3$); −0.11 (SiMe$_2$Ph); 0.80 (SiMe$_3$); $^{29}$Si NMR (119.23 MHz, $C_6D_6$, 300 K) δ (ppm) = −18.68 (SiMe$_3$); −22.98 (SiMe$_2$Ph). |

TABLE 1-continued

Characterization of the compounds obtained in the Examples.

| Example | Name | Elemental analysis + NMR analysis |
|---|---|---|
| 10 | 1,3-bis(trimethylsilyl-ethynyl)-1,1,3,3-tetramethyldisiloxane | Analysis calculated for $C_{14}H_{30}OSi_4$: C 51.46; H 9.25; found C 51.54; H 9.28; $^1H$ NMR (300 MHz, CDCl$_3$, 300 K) δ (ppm) = 0.27 (s, 12H, SiMe$_2$); 0.18 (s, 18H, SiMe$_3$); $^{13}C$ NMR (75.45 MHz, C$_6$D$_6$, 300 K) δ (ppm) = 112.99 ($\underline{C}$≡C—SiMe$_3$); 2.06 (SiMe$_2$); −0.25 (SiMe$_3$); $^{29}Si$ NMR (119.23 MHz, C$_6$D$_6$, 300 K) δ (ppm) = −18.11 (SiMe$_2$); −18.65 (SiMe$_3$). |
| 11 | 1,2-(bis(trimethylsilyl-ethynyl)dimethylsilyl)ethane | Analysis calculated for $C_{16}H_{34}Si_4$: C 56.72; H 10.12; found C 56.71; H 10.15; $^1H$ NMR (300 MHz, CDCl$_3$, 300 K) δ (ppm) = 0.58 (s, 4H, —CH$_2$—); 0.17 (s, 18H, SiMe$_3$); 0.15 (s, 12H, SiMe$_3$); $^{13}C$ NMR (75.45 MHz, C$_6$D$_6$, 300 K) δ (ppm) = 114.42 ($\underline{C}$≡C—SiMe$_3$); 113.03 (C≡$\underline{C}$—SiMe$_3$); 8.30 (—CH$_2$—); −0.04 (SiMe$_3$); −2.34 (SiMe$_2$); $^{29}Si$ NMR (119.23 MHz, C$_6$D$_6$, 300 K) δ (ppm) = −15.10 (SiMe$_2$); −19.13 (SiMe$_3$). |
| 12 | 1,4-bis(trimethylsilyl-ethynyl)benzene | Analysis calculated for $C_{16}H_{22}Si_2$: C 71.04; H 8.10; found C 71.12; H 8.13; $^1H$ NMR (300 MHz, CDCl$_3$, 300 K) δ (ppm) = 7.39 (s, 4H, —C$_6$H$_4$—); 0.24 (s, 18H, —SiMe$_3$); $^{13}C$ NMR (75.45 MHz, C$_6$D$_6$, 300 K) δ (ppm) = 131.73 ($\underline{C}$—H); 123.11 ($\underline{C}$≡C—SiMe$_3$); 96.28 (C≡$\underline{C}$—SiMe$_3$); 95.10 (C≡$\underline{C}$—SiMe$_3$); −0.11 (SiMe$_3$); $^{29}Si$ NMR (119.23 MHz, C$_6$D$_6$, 300 K) δ (ppm) = −17.51 (SiMe$_3$). |
| 13 | bis(trimethylsilylethynyl)phenylmethylsilane | Analysis calculated for $C_{17}H_{26}Si_3$: C 64.89; H 8.33; found C 65.04; H 65.14; $^1H$ NMR (300 MHz, CDCl$_3$, 300 K) δ (ppm) = 7.73 (m, 2H, m-Ph); 7.40 (m, 3H, o,p-Ph); 0.54 (s, 3H, Si—Me); 0.21 (s, 18H, SiMe$_3$); $^{13}C$ NMR (75.45 MHz, C$_6$D$_6$, 300 K) δ (ppm) = 134.09; 129.91; 127.92 (Ph); 117.16 (Si—$\underline{C}$≡C—SiMe$_3$); 107.78 (Si—C≡$\underline{C}$—SiMe$_3$); 0.22 (Si—Me); −0.28 (SiMe$_3$); $^{29}Si$ NMR (119.23 MHz, C$_6$D$_6$, 300 K) δ (ppm) = −17.94 (SiMe$_3$); −46.91 (Si—Ph). |
| 14 | bis(trimethylsilylethynyl)diphenylsilane | Analysis calculated for $C_{22}H_{28}Si_3$: C, 70.14; H, 7.49; found C 70.23; H 7.52; $^1H$ NMR (300 MHz, CDCl$_3$, 300 K) δ (ppm) = 7.75 (m, 4H, m-Ph); 7.40 (m, 6H, o,p-Ph); 0.23 (s, 18H, SiMe$_3$); $^{13}C$ NMR (75.45 MHz, C$_6$D$_6$, 300 K) δ (ppm) = 134.79; 132.82; 130.10; 127.95 (Ph); 118.97 (Si—$\underline{C}$≡C—SiMe$_3$); 106.12 (Si—C≡$\underline{C}$—SiMe$_3$); −0.31 (SiMe$_3$); $^{29}Si$ NMR (119.23 MHz, C$_6$D$_6$, 300 K) δ (ppm) = −17.54 (SiMe$_3$); −51.33 (SiPh$_2$). |
| 15 | 1-(N,N-bis(trimethylsilyl)-amino)-3-trimethylsilylprop-2-yne | Analysis calculated for $C_{12}H_{29}NSi_3$: C 53.06; H 10.76; N 5.16; found C 53.37; H 9.70; N 5.43; $^1H$ NMR (300 MHz, CDCl$_3$, 300 K) δ (ppm) = 3.45 (s, 2H, —CH$_2$—); 0.19 (s, 18H, N(SiMe$_3$)$_2$); 0.16 (s, 9H, —SiMe$_3$); $^{13}C$ NMR (75.46 MHz, C$_6$D$_6$, 300 K) δ (ppm) = 109.59 ($\underline{C}$≡C—SiMe$_3$); 86.78 (C≡$\underline{C}$—SiMe$_3$); 35.54 (—CH$_2$—); 2.21 (—N(SiMe$_3$)$_2$); 0.04 (—SiMe$_3$); $^{29}Si$ NMR (119.23 MHz, C$_6$D$_6$, 300 K) δ (ppm) = 8.12 (N(SiMe$_3$)$_2$); −19.12 (—SiMe$_3$). |
| 16, 17 | 1-(3-N,N-bis(trimethylsilyl)-aminophenyl)-2-trimethylsilylethyne | Analysis calculated for $C_{17}H_{31}NSi_3$: C 61.19; H 9.36; N 4.20; found C 78.17; H 9.60; N 4.5; $^1H$ NMR (300 MHz, CDCl$_3$, 300 K) δ (ppm) = 7.18 (s, 1H, —C$_6$H$_4$—); 6.81 (t, 1H, —C$_6$H$_4$—); 6.67 (m, 1H, —C$_6$H$_4$—); 0.14 (s, 9H, —SiMe$_3$); −0.06 (s, 18H, —N(SiMe$_3$)$_2$); $^{13}C$ NMR (74.46 MHz, C$_6$D$_6$, 300 K) δ (ppm) = 148.50; 133.63; 128.94; 124.30 (—C$_6$H$_4$—); 106.07 ($\underline{C}$≡C—SiMe$_3$); 94.02 (C≡$\underline{C}$—SiMe$_3$); 2.49 (—N(SiMe$_3$)$_2$); 0.44 (—SiMe$_3$); $^{29}Si$ NMR (119.23 MHz, C$_6$D$_6$, 300 K) δ (ppm) = 4.88 (—N(SiMe$_3$)$_2$); −18.15 (—SiMe$_3$). |
| 18, 19 | 4-(trimethylsilylethynyl)biphenyl | Analysis calculated for $C_{17}H_{18}Si$: C 81.54; H 7.25; found C 81.58; H 7.27; $^1H$ NMR (300 MHz, CDCl$_3$, 300 K) δ (ppm) = 7.60 (d); 7.59 (d); 7.57 (m); 7.55 (s); 7.45 (t); 7.37 (qt) (9H, Ph—C$_6$H$_4$—); 0.28 (s, 9H, —SiMe$_3$); $^{13}C$ NMR (75.46 MHz, C$_6$D$_6$, 300 K) δ (ppm) = 141.11; 140.25; 132.25; 128.81; 127.98; 126.83; 121.94; 104.93 ($\underline{C}$≡C—SiMe$_3$); 94.82 (C≡$\underline{C}$—SiMe$_3$); −0.02 (—SiMe$_3$). |
| 20, 21 | 1-(trimethylsilylethynyl)naphthalene | Analysis calculated for $C_{15}H_{16}Si$: C 80.30; H 7.19; found C 80.40; H 7.22; $^1H$ NMR (300 MHz, CDCl$_3$, 300 K) δ (ppm) = 8.35 (dm, 1H); 7.84 (tm, 2H); 7.71 (dd, 1H); 7.55 (dt, 1H); 7.41 (dd, 1H); 0.35 (s, 9H, —SiMe$_3$); $^{13}C$ NMR (74.46 MHz, C$_6$D$_6$, 300 K) δ (ppm) = 133.35; 133.03; 130.77; 128.95; 128.22; 126.79; 126.35; 126.16; 125.08; 120.68 (C$_{10}$H$_7$—); 103.00 ($\underline{C}$≡C—SiMe$_3$); 99.41 (C≡$\underline{C}$—SiMe$_3$); 0.10 (—SiMe$_3$). |

TABLE 1-continued

Characterization of the compounds obtained in the Examples.

| Example | Name | Elemental analysis + NMR analysis |
|---|---|---|
| 22, 23 | 2-(4-trimethylsilylethynyl-phenyl)-4,4,5,5-tetramethyl-1,3,2-dioxoborate | Analysis calculated for $C_{17}H_{25}BO_2Si$ C 68.00; H 8.39; found C 68.15; H 8.42; $^1$H NMR (300 MHz, CDCl$_3$, 300 K) δ (ppm) = 7.73 (d, 2H, —C6H4—); 7.46 (d, 2H, —C$_6$H$_4$—); 1.31 (s, 12H, —Me$_2$C—CMe$_2$—); 0.18 (s, 9H, OSiMe$_3$); 0.07 (s, 9H, SiMe$_3$); $^{13}$C NMR (75.45 MHz, C$_6$D$_6$, 300 K) δ (ppm) = 134.40; 131.25; 131.07; 125.69; 105.11; 95.52; 83.93; 24.85; −0.08 (—SiMe$_3$); |
| 24, 25 | 1-(4-N,N-bis(trimethylsilyl)-aminophenyl)-2-trimethylsilylethyne | Analysis calculated for $C_{17}H_{31}NSi_3$ C 61.19; H 9.36; found C 62.22; H 9.38; $^1$H NMR (300 MHz, CDCl$_3$, 300 K) δ (ppm) = 7.24 (d, 2H, —C$_6$H$_4$—); 6.73 (d, 2H, —C$_6$H$_4$—); 0.16 (s, 9H, —SiMe$_3$); 0.03 (s, 18H, —N(SiMe$_3$)$_2$); $^{13}$C NMR (75.45 MHz, C$_6$D$_6$, 300 K) δ (ppm) = 149.12; 132.42; 129.93; 118.03; 105.42; 93.30; 2.11 (—NSiMe$_3$); 0.11 (—SiMe$_3$). |

The invention claimed is:

1. (Triorganosily)alkynes, having the general formula 1, $$R^1\text{—}C\equiv C\text{—}Z \qquad (1)$$

in which
  $R^1$ denotes —$SiR^2R^3R^4$ where $R^2R^3R^4$ are equal and denote a $C_{1-5}$ alkyl group or phenyl,
  Z denotes 3-N,N-bis(trimethylsilylamino)phenyl, or 4-N,N-bis(trimethylsilylamino)phenyl.

2. A method to obtain (triorganosilyl)alkynes having the general formula 1, $$R^1\text{—}C\equiv C\text{—}Z \qquad (1)$$

in which
  $R^1$ denotes —$SiR^2R^3R^4$ where $R^2R^3R^4$ are equal and denote
    a $C_{1-5}$ alkyl, or,
    a phenyl,
  Z denotes 3-N,N-bis(trirnethylsilylamino)phenyl, or 4-N,N-bis(trimethylsilylamino)phenyl,
  wherein it consists in reacting a suitable terminal alkyne having the general formula 9, $$H\text{—}C\equiv C\text{—}Z \qquad (9)$$

in which Z denotes the same as stated above,
and a suitable halo genotriorganosilane having the general formula 10, $$X\text{—}R^1 \qquad (10)$$

in which
  X denotes Cl, Br, I,
  $R^1$ denotes the same as stated above, in the presence of an iridium catalyst having the general formula 4, $$[\{Ir(\mu\text{-}Cl)(L)\}_2], \qquad (4)$$

in which L denotes $(CO)_2$ or cis, cis-1,5-cyclooctadiene (cod),
and a tertiary amine having the general formula 5 in which $$NA^1A^2A^3 \qquad (5)$$

in which
  $A^1A^2A^3$ are equal or different and denote a $C_{1-5}$ alkyl, a $C_{5-7}$ cycloalkyl, an aryl, an arylalkyl where the alkyl chain contains $C_{1-4}$, an alkylaryl where the alkyl chain contains $C_{1-4}$, so that none of the substitutes is a heteroaryl or a heteroaryl derivative.

3. A method as claimed in claim 2 wherein the iridium complex used is $[\{Ir(\mu\text{-}Cl)(CO)_2\}_2]$.

4. A method as claimed in claim 2 wherein the iridium complex is used in an amount in the range from 0.01 to 4 mol% relative to the functional terminal alkyne group.

5. A method as claimed in claim 4 wherein the iridium complex is used in an amount in the range from 0.5 to 1 mol% relative to the functional terminal alkyne group.

6. A method as claimed in claim 4 wherein, in the synthesis of the compounds containing an amine substitute, the iridium complex is used in an amount in the range from 0.5 to 2 mol % relative to the functional terminal alkyne group.

7. A method as claimed in claim 2, wherein the amine having the formula 5 is used in an amount not smaller than that equivalent to the sum of a stoichiometric amount of the hydrogen halide formed and a 2.2-fold excess relative to the iridium ion in the complex used.

* * * * *